United States Patent [19]

Monroe

[11] 4,432,372
[45] Feb. 21, 1984

[54] TWO-LEAD POWER/SIGNAL MULTIPLEXED TRANSDUCER

[75] Inventor: Paul P. Monroe, Janesville, Wis.

[73] Assignee: Medtronic, Inc., Minneapolis, Minn.

[21] Appl. No.: 297,472

[22] Filed: Aug. 28, 1981

[51] Int. Cl.³ .............................................. A61B 5/02
[52] U.S. Cl. ................................................ 128/675
[58] Field of Search ............... 128/673, 675, 736, 902, 128/748; 73/719–721, 725–727; 324/57 PS, 57 Q

[56] References Cited

U.S. PATENT DOCUMENTS

| 3,076,338 | 2/1963 | Peltola | 324/57 PS |
|---|---|---|---|
| 3,154,066 | 10/1964 | Grindheim et al. | 73/726 X |
| 3,350,944 | 11/1967 | DeMichele | 128/748 X |
| 3,473,386 | 10/1969 | Nielsen, Jr. et al. | 73/398 |
| 3,545,275 | 12/1970 | Harrison et al. | 128/675 |
| 3,614,954 | 10/1971 | Mirowski et al. | 128/419 |
| 3,786,348 | 1/1974 | Lynas et al. | 324/57 PS |
| 4,023,562 | 5/1977 | Hynecek et al. | 128/2.05 E |
| 4,114,606 | 9/1978 | Seylar | 128/748 X |
| 4,237,900 | 12/1980 | Schulman et al. | 128/673 X |
| 4,312,361 | 1/1982 | Nicholson et al. | 128/748 |

FOREIGN PATENT DOCUMENTS

| 132701 | 10/1978 | Fed. Rep. of Germany | 128/673 |
| 200239 | 9/1967 | U.S.S.R. | 73/725 |

OTHER PUBLICATIONS

"Minature Pressure Transducer for Biomedical Applications" by Jaroslav Hynecek, pp. 137–165 of the book *Indwelling and Implantable Pressure Transducers*, by D. G. Fleming et al., 1977.
Fryer, T. B., "Capacitance Pressure Transducers", pp. 173–181 of book *Indwelling & Implantable Pressure Transducers*, D. G. Fleming et al., CRC Press, Cleveland, 1977.
Borky, J. M. et al., "Integrated Signal Conditioning for Silicon Pressure Sensors", *IEEE Trans. on Electron Devices*, Vol. ED-26, #12, Dec. 1979, pp. 1906–1910.
Hok, B., "New Microtransducer for Physiological Pressure Recording", MBE vol. 13, #2, pp. 279–284, Mar. 1975.
Delannois, A. L., "Low Cost IC Transducer for Med. Pressure Measurements", MBE vol. 12, No. 3, May, 1974, pp. 364–365.

*Primary Examiner*—Kyle L. Howell
*Assistant Examiner*—Francis J. Jaworski
*Attorney, Agent, or Firm*—Reed A. Duthler; John L. Rooney; Joseph F. Breimayer

[57] ABSTRACT

Technique of and apparatus for multiplexing the power and signal leads of an implantable piezoresistive pressure transducer. A semiconductor switching circuit multiplexes the two leads between the transducer element and the electronic processing element. During the charge cycle, the switching circuit connects the power source to the two leads. The power source charges a capacitor located within the resistive bridge of the piezoresistive transducer. A sensing cycle causes the switching circuitry to remove the power source from the two leads, and to switch the two leads to the input circuit of the sensing electronics. Optional steering diodes may be employed in the resistive bridge to minimize heating of two of the resistors caused by charging current. The sensing circuit employs a sample and hold technique so that the sensed output is supplied constantly over time without the interruptions caused by the switching circuit action of charging the capacitor within the resistive bridge.

13 Claims, 5 Drawing Figures

TWO-LEAD POWER/SIGNAL MULTIPLEXED TRANSDUCER

CROSS REFERENCE TO CO-PENDING APPLICATION

Attention is drawn to U.S. patent application Ser. No. 186,373 filed Sept. 12, 1980 entitled "Integral Hermetic Implantable Pressure Transducer" assigned to the assignee of the present invention.

BACKGROUND OF THE INVENTION

1. Field of the Invention

The present invention relates generally to implantable transducers and more particularly relates to implantable transducers having a resistive bridge physically remote from the sensing electronics.

2. Description of the Prior Art

The earliest and, indeed, the currently most prevalent type of pressure measurement systems to be used within the human body use a pressure transmitting catheter which transmits the pressure to be measured between a remote site located within the body and the pressure transducer itself which is located external to the body. Such an apparatus is described in U.S. Pat. No. 3,473,386 issued to Nielsen Jr., et al. The primary disadvantage of this technique is the lack of accuracy achieved by the pressure transmitting catheter. A second disadvantage now becoming prominent is that devices of this type are not implantable and are therefore not suitable for chronic applications.

An early disclosure of an application for a chronically implantable pressure transducer is seen in U.S. Pat. No. 3,614,954 issued to Mirowski et al. The pressure transducer envisioned by Mirowski et al is a piezoresistive bridge circuit. Referring to FIG. 3 of Mirowski et al, one can see the pressure transducer element diagrammed as reference number 40. It is observed that the pressure transducer is a standard four-leg resistive bridge having two connections for supplying power noted −IV and +IV and having two signal connections which are connected to amplifier circuit 42. Though this is a relatively early technique, it is still the most popular technique for connecting an implantable pressure transducer to the associated electronics.

A much later transducer is disclosed in U.S. Pat. No. 4,023,562 issued to Hynecek et al. This reference describes, in considerable detail, the structure of an implantable piezoresistive silicon-based pressure transducer. However, notice at FIG. 1 the four connections that are required. These are brought out to the four metallized conductor pads 9. The specification at column 3, lines 48–50 states, "external readout equipment (not shown) is connected to the external transducer contacts 9 by the wires 12 (FIG. 2)". Hynecek et al. definitely envisioned four separate conductors.

U.S. patent application Ser. No. 186,373 entitled Integral Hermetic Implantable Pressure Transducer by Kenneth M. Anderson filed Sept. 12, 1980 assigned to the assignee of the present patent application discloses a practical, chronically implantable pressure transducer with a hermetically sealed package. Again, the pressure transducer taught by Anderson uses a four-wire system. Two of the wires are used to supply the power to the resistive bridge and the remaining two conductors are used for sensing.

It is desirable to minimize the number of conductors required because this decreases the diameter of the lead required for implantation and increases the reliability over time.

SUMMARY OF THE INVENTION

The present invention uses a hermetically sealed silicon-based piezoresistive pressure transducer coupled via a body implantable lead to sensing circuitry. By employing a switching circuit near the sensing electronics, along with a capacitor and optional steering diodes within the resistive bridge, two conductors may be multiplexed or time-shared between the two functions of supplying power to the resistive bridge and sensing the resulting changes in resistivity.

The switching circuit supplies power via the two conductors for a portion of each sensing cycle. The power is steered to the capacitor charging it for later use. During the charging portion of the cycle, the sensing circuitry is removed from the two multiplexed conductors. During the second portion of the cycle, the power source is disconnected from the two conductors, and the two conductors are connected to the input of the sense circuit. At this point in time, the capacitor within the resistive bridge discharges through the resistive bridge and changes in resistivity may then be measured by the sensing circuit.

A sample and hold circuit may be employed within the sensing electronics. This circuit enables the sensing electronics to output a constant value indicative of the pressure sensed by the pressure transducer as integrated over the entire sensing cycle. This sample and hold circuitry thereby enables other circuitry to utilize the pressure transducer output as if it came from the normal four-wire system as is commonly found in the art.

DETAILED DESCRIPTION OF THE PREFERRED EMBODIMENT

The preferred embodiment of the present invention is disclosed as incorporated within a chronically implantable pressure transducer. The pressure transducer is a piezoresistive silicone device electrically viewed as a resistive bridge circuit. From the foregoing description it will become apparent to those of ordinary skill in the art that the present invention could be applied to other types of implantable sensors measuring other types of parameters.

Figure 1:
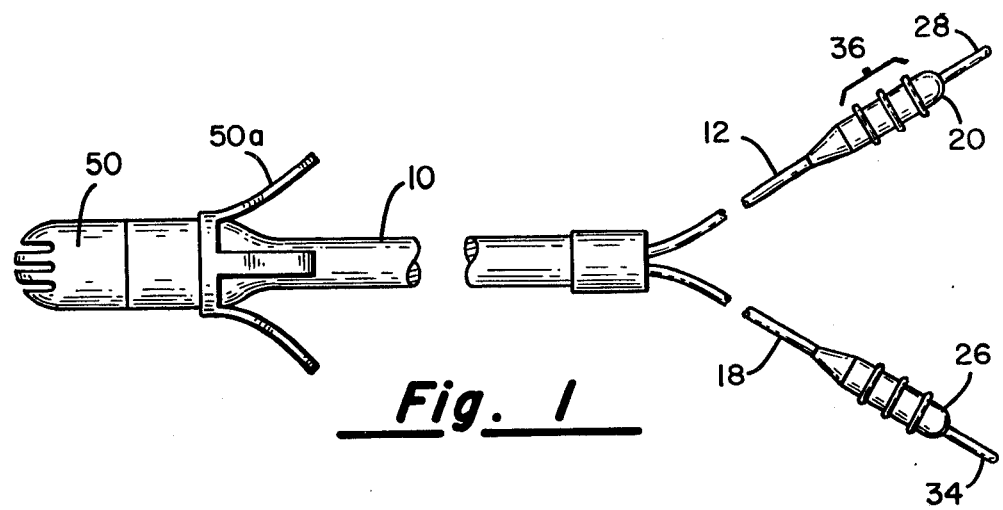
FIG. 1 is a plan view of a body implantable lead containing a pressure transducer utilizing a two-wire transmission technique.

FIG. 1 is a plan view of a chronically implantable lead employing the present invention. The pressure transducer head is found at the distal end. It is covered by protective dome 50 which insures that the pressure transducer element is not damaged during the implantation procedure. The preferred method of the packaging the pressure transducer is described in detail in the above-referenced patent application of Kenneth M. Anderson assigned to the assignee of the present invention. However, other means of packaging as discussed in the other references may also be employed. Tines 50a are located near the pressure transducer head and provide for acute fixation.

Lead body 10 is covered by a body compatible insulating sheath which protects the two inner conductors. Preferably, the two conductors are coils wound coaxially or are mutually insulated multifilar coils wound about the same axis having a similar diameter. The individual conductors appear at the proximal end as separate, insulated conductors 12 and 18. Conductor 12 terminates in electrical connector 20 having terminal pin 28. Similarly, conductor 18 terminates at electrical connector 26 having electrically conductive terminal pin 34. As can be seen, the sealing rings 36 enable the connectors to be sealed against the female connection of the implantable medical device.

Figure 2:
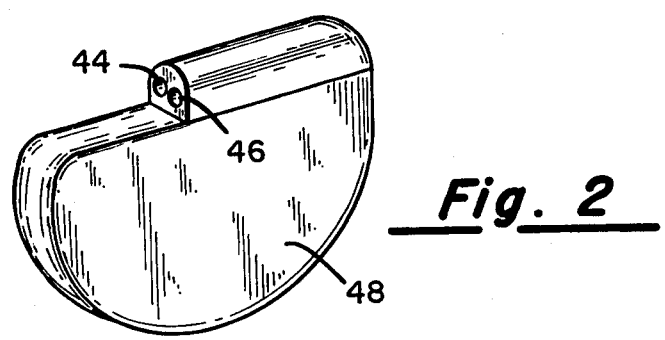
FIG. 2 is a plan view of an implantable pulse generator which is connected to the body implantable lead of FIG. 1.

FIG. 2 is a plan view of a pulse generator housing the switching and sample and hold circuitry. The main body of pulse generator 48 contains female connector slots 44 and 46 into which connector pins 20 and 26 are inserted (see also FIG. 1).

Figure 3:
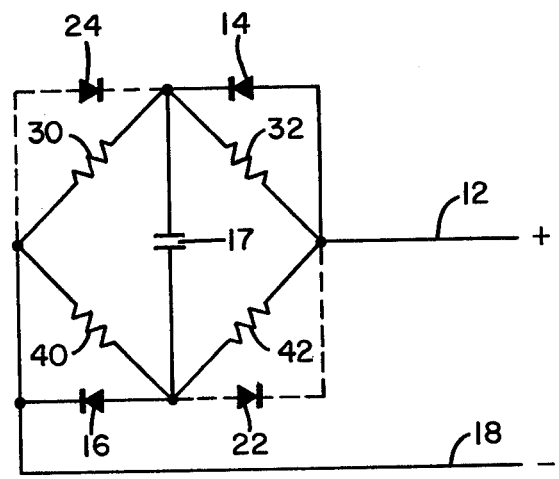
FIG. 3 is an electrical schematic diagram of the piezoresistive bridge circuit including the multiplexing capacitor and steering diodes.

FIG. 3 is an electrical schematic diagram of the pressure transducer head. Notice that it appears as a resistive bridge having resistors 30, 32, 40 and 42. As is common in the art, the values of these resistors change relative to one another with changes in pressure allowing the sensing circuitry to thereby sense pressure changes impinging upon the transducer.

In a typical practical system, the bridge circuit of FIG. 3, including resistors 30, 32, 40 and 42 is purchasable as a monolithic device on a silicon substrate as disclosed by Hynecek et al. in U.S. Pat. No. 4,023,562. Capacitor 17 has a value of approximately 0.01 microfarads. Diodes 14, 16, 22 and 24 are typical silicon devices of type 1N4148.

Figure 4:
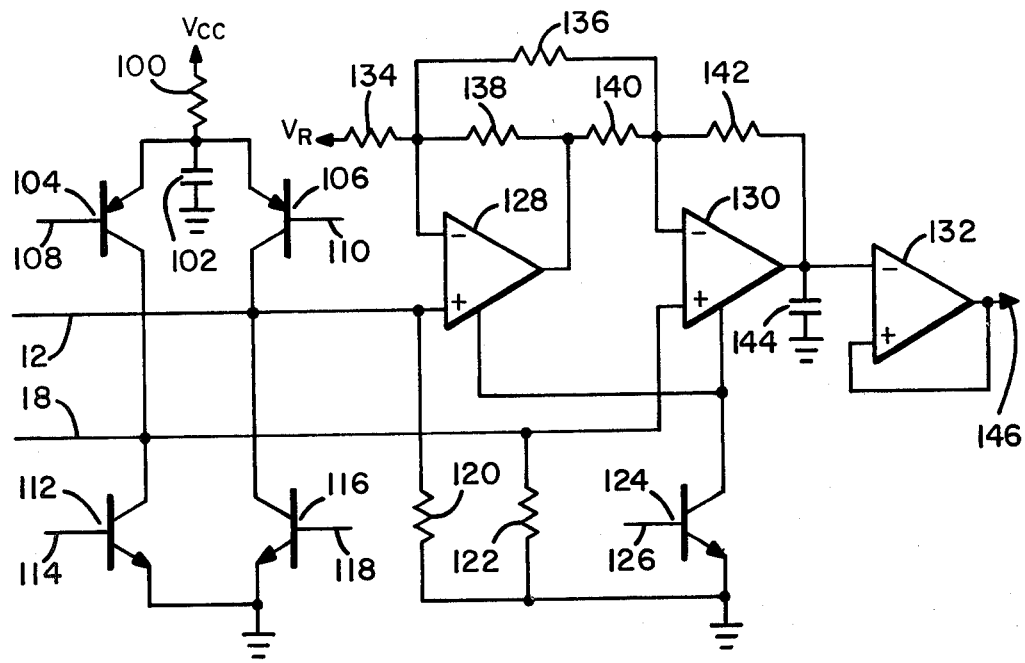
FIG. 4 is a schematic diagram of the switching circuitry and the sample and hold circuit used at the proximal end of the body implantable lead.

During the charging portion of the operating cycle of the circuit of FIG. 4, current flows from the switching circuit through conductors 12 and 18 to charge capacitor 17.

During the first charging portion of the cycle, current flows from conductor 12 through diode 14 and to capacitor 17. Return flow is from capacitor 17 via diode 16 to conductor 18. On the alternate charging cycle, current flows from conductor 18 through optional diode 24 to capacitor 17. Return flow is from capacitor 17 through alternate diode 22 to conductor 12. This is done to equalize heating effects on resistors 30, 32, 40, and 42. However, capacitor 17 is always charged to the same polarity represented by the "+" at conductor 12 and the "−" at conductor 18.

Optional diodes 22 and 24 are employed to effectively shunt the current past resistors 30 and 42 during the alternate charging cycle. These optional diodes are necessary only if it is anticipated that resistors 30 and 42 will be experience substantial heating relative to resistors 32 and 40.

FIG. 4 is a schematic diagram of the switching circuit and sample and hold circuit. The circuitry of FIG. 4 is used to time-share conductors 12 and 18 which couple implantable pulse generator 48 to the transducer head circuitry of FIG. 3. This multiplexing is accomplished by alternately switching power to charge capacitor 17 and removing power to sense the discharge of capacitor 17 through the resistance bridge of the pressure transducer. Because of the diodes of FIG. 3, capacitor 17 is charged to the same polarity each time even though the circuitry of FIG. 4 alternately applies opposite polarities to conductors 12 and 18.

During a first charging portion of the cycle, transistor 104 is caused to shut off and transistor 106 is caused to conduct. This places voltage Vcc through resistor 100 onto conductor 12 causing it to be a current source to charge capacitor 17 (see also FIG. 3). Simultaneously, transistor 112 is also caused to conduct, thereby grounding conductor 18 and completing the circuit. As can be seen therefore, the charging circuit proceeds from +Vcc through resistor 100 through conducting transistor 106 and through conductor 12. Referring to FIG. 3, conductor 12 then supplies current through diode 14 to charge the positive side of capacitor 17. Similarly, the return circuit is from capacitor 17 through diode 16 and back through the body implantable lead via conductor 18. Referring again to FIG. 4, the return current path of conductor 18 proceeds through conducting transistor 112 to ground. This completes the operation of a first charging portion of the cycle.

Following the first charging portion of the cycle, transistors 104, 106, 112 and 116 are all biased to a nonconducting state. This makes conductors 12 and 18 a high impedance input circuit for the sensing circuitry.

During the sensing portion of the cycle, transistor 124 is caused to conduct to ground, thereby enabling operational amplifiers 128 and 130 to operate within their linear range. During the time when they are turned on, operational amplifiers 128 and 130 are caused to slew towards their equilibrium value by the signal across conductors 12 and 18 caused by the discharge of capacitor 17 through the resistive bridge, and by the reference offset value of $V_R$. The output of amplifier 130 charges capacitor 144 during that period of time in which transistor 124 is conducting. Subsequently, transistor 124 is turned off, removing the bias from operational amplifiers 128 and 130. This leaves the operational amplifiers in a high impedance state, thereby causing capacitor 144 to hold a voltage proportional to the sensed signal generated by the resistance bridge. Operational amplifier 132 thereby supplies an output at line 146 which is proportional to the charge stored within capacitor 144. During each charging portion of the cycle, the voltage output at line 146 is proportional to the previously sensed value as stored by capacitor 144. Thus, it can be seen that operational amplifier 132 applies a constant output via output line 146 even though the sensing of the value of the resistive bridge takes place only during a portion of the total cycle.

The alternate charging cycle charges capacitor 17 using current flowing from Vcc and resistor 100 through conductor 18 with return flow via conductor 12. This happens when transistors 104 and 116 are biased to conduction. This means that Vcc supplies a positive current across resistor 100 and through conducting transistor 104 to conductor 18. Referring again to FIG. 3, this positive voltage on conductor 18 back biases diode 16 causing it not to conduct. Current thus flows through resistor 30 (or optional diode 24) to charge capacitor 17 with the same polarity as the previous charging cycle. The return path from capacitor 17 is via resistor 42 (or optional diode 22) to conductor 12.

Referring again to FIG. 4, it can be seen that conductor 12 is grounded via conducting transistor 116.

Figure 5:
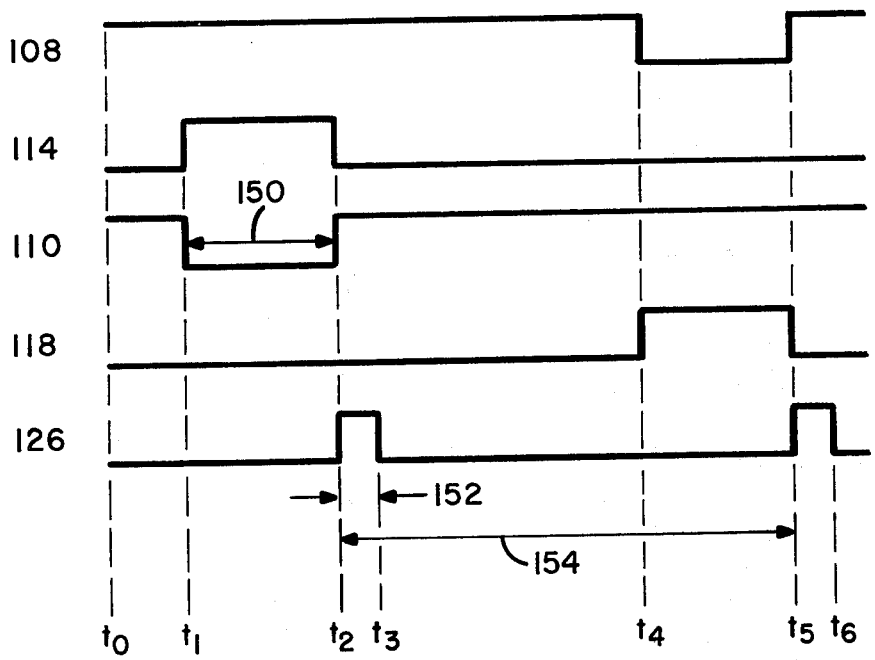
FIG. 5 is a timing diagram showing control signals applied to the circuit of FIG. 4 for powering the transducer during a first portion of the operating cycle of the system and for sensing the resulting pressure signal during a second sensing portion of the cycle.

FIG. 5 is a timing diagram showing the signals required to control the proper operation of the disclosed circuitry during two successive cycles. Lines 108, 114, 110, 118, and 126 depict signals which are applied to the like-numbered conductors in FIG. 4 to control the charging and sensing operations of the multiplexing circuit during each cycle. Line 108 is the control input to the base of transistor 104 which is a PNP-type transistor. Notice that line 108 remains high thereby cutting off transistor 104 at all times, except between time T4 and T5 as shown in FIG. 5. This is the time at which line 118 is also positive. As can be seen in FIG. 4, this causes NPN transistor 116 to also conduct. Therefore, between time periods T4 and T5 conductors 12 and 18 are connected in the alternate charging configuration.

The charging portion of the first cycle depicted in FIG. 5 occurs during time T1 through time T2 (denoted 150) at which time line 114 is positive and line 110 is negative. During time 150 the signal on line 114 causes NPN transistor 112 to clamp conductor 18 to ground and the signal on line 110 causes PNP transistor 106 to conduct current between +Vcc through resistor 100 to conductor 12. Capacitor 102 is a large capacitor on the order of 10 microfarads. This insures that, for the charging portion of the cycle, conductors 12 and 18 experience a relatively constant voltage potential ensuring a constant and known charge accumulation in capacitor 17.

Referring again to FIG. 5, the signal on the remaining control line 126 goes positive for time 152 between time T2 and T3. Referring again to FIG. 4, transistor 124 conducts in response to the positive signal occurring during time 152, thereby biasing operational amplifiers 128 and 130 to a conducting state. The time between T2 and T3 is that time in which sampling eventually occurs and the discharge of capacitor 17 through the resistive bridge is at it most linear point. The time between times T2 and T5 is the time during which the output (shown as 154) represents a constant output of operational amplifier 132 because of the charging of capacitor 144 which holds the value during the time T3 through T5. At T5, transistor 124 is again biased to conduction charging capacitor 144 to a new value until time T6. The first charging cycle is then repeated.

Referring to FIG. 4, +Vcc is preferably on the order of 2.8 volts. Resistor 100 is chosen to give a total charging resistance of about 5k ohms. As stated above, capacitor 102 is chosen to be on the order of 10 microfarads to insure a constant charging voltage. It has been found that a charging time (i.e., time 150 from T1 to T2) is on the order of 1½ micro seconds. Transistors 106 and 108 are typical PNP transistors, whereas transistors 114 and 116 are typical NPN transistors.

A sampling rate of 1 kilohertz was chosen as being convenient for the present application. Operational amplifiers 128 and 130 are chosen to be of commonly available part LM146. A total sample plus slew time, time 154 on FIG. 5, (i.e., time T2 through T5) is on the order of 4 micro seconds. Time 152 between T2 and T3 is the sample gate time which is on the order of 0.5 micro seconds. Capacitor 144 has the convenient value of 0.001 microfarads. Operational amplifier 132 is a model LM146. Reference voltage $V_R$ has a value of 1.4 volts.

Having thus described the present invention in relation to a specific application of an implantable pressure transducer, those of ordinary skill will be readily able to apply the teachings found herein to other transducer configurations.

What is claimed is:

1. A body implantable transducer assembly comprising:
    a transducer head requiring an electrical power input and supplying an electrical output signal and comprising a piezoresistive resistance bridge having a temporary storage means whereby said electrical output signal is generated by said electrical power input as stored in said temporary storage means passing through said piezoresistive resistance bridge;
    means for processing said electrical output signal;
    means responsively coupled to said transducer head and said processing means for conducting said electrical output signal between said transducer head and said processing means; and
    means responsively coupled to said conducting means for supplying said electrical power input to said transducer head via said conducting means.

2. A body implantable transducer assembly according to claim 1 wherein said conducting means comprises two conducting paths.

3. A body implantable transducer assembly according to claim 2, wherein said supplying means further comprises:
    a power supply; and
    means responsively coupled to said two conducting paths for alternate switching to couple said power supply to said temporary storage means for a first period of time and to couple said piezoresistive resistance bridge to said processing means for a second period of time.

4. A body implantable transducer assembly according to claim 3 wherein said temporary storing means comprises a capacitor.

5. A body implantable transducer assembly according to claim 4 wherein said processing means further comprises a sample and hold circuit whereby a simulated output signal is generated representative of said electrical output signal during said first period of time and during said second period of time.

6. A body implantable transducer assembly according to claim 5 wherein said two conducting paths comprise two wires.

7. A body implantable transducer assembly, comprising:
    a transducer head including a transducer comprising a piezoresistive resistance bridge requiring an electrical power input and supply an electrical output signal concurrent with said electrical power input and storage means for storing an electrical power input and for providing said electrical power input as stored, to said transducer; and
    conductor means consisting of two conductors coupled to said transducer head for conducting said electrical power input to said storage means and for conducting said electrical output signal from said transducer.

8. A body implantable transducer assembly according to claim 7, further comprising power supply means for supplying said electrical power input to said storage means during a first time period; and
    processing means for processing said electrical output signal from said transducer head during a second time period, subsequent to said first time period.

9. A body implantable transducer assembly according to claim 8 wherein said processing means further comprises a sample and hold means for generating a simulated output signal representative of said electrical output signal during said first period of time and during said second period of time.

10. A body implantable transducer assembly according to claim 8 wherein said power supply means provides said electrical power input during said first time period at a first polarity, and at a second polarity during a third time period following said second time period, and wherein said processing means further processes said electrical output signal from said transducer during a fourth time period, following said third time period.

11. A body implantable transducer assembly according to claim 10 wherein said transducer head further comprises first steering diode means, coupled to said storage means for applying said electrical power input to said storage means during said first time period and second steering diode means coupled to said storage means for applying said electrical power input signal to said storage means during said third time period.

12. A body implantable transducer assembly according to claim 8 wherein said transducer head further comprises steering diode means for applying said electrical power input to said storage means during said first time period.

13. A body implantable transducer assembly according to claim 7 wherein said storage means comprises a capacitor.

* * * * *